United States Patent
Bonnert et al.

[11] Patent Number: 5,929,100
[45] Date of Patent: *Jul. 27, 1999

[54] BIOLOGICALLY ACTIVE BENZOTHIAZOLONE ETHANAMINES

[75] Inventors: Roger Bonnert, Hoton; Roger Brown, Loughborough; Peter Cage, Shepshed; David Cheshire, Chilwell; Francis Ince, Loughborough, all of United Kingdom

[73] Assignee: Astra Pharmaceuticals Limited, Herts, United Kingdom

[ * ] Notice: This patent is subject to a terminal disclaimer.

[21] Appl. No.: 08/793,706
[22] PCT Filed: Dec. 13, 1996
[86] PCT No.: PCT/SE96/01650
    § 371 Date: Mar. 3, 1997
    § 102(e) Date: Mar. 3, 1997
[87] PCT Pub. No.: WO97/23470
    PCT Pub. Date: Jul. 3, 1997

[30] Foreign Application Priority Data

Dec. 23, 1995 [GB] United Kingdom ................ 9526511

[51] Int. Cl.⁶ ........................ A61K 31/425; C07D 277/68
[52] U.S. Cl. ........................ 514/367; 548/169; 548/171
[58] Field of Search ................ 548/169, 171; 514/367

[56] References Cited

U.S. PATENT DOCUMENTS

| 5,648,370 | 7/1997 | Bonnert et al. ................ 514/367 |
| 5,763,465 | 6/1998 | Bonnert et al. ................ 514/367 |

FOREIGN PATENT DOCUMENTS

| 0 046 666 | 8/1981 | European Pat. Off. . |
| 0 113 964 | 11/1983 | European Pat. Off. . |
| 0 174 811 | 9/1985 | European Pat. Off. . |
| 0 175 525 | 9/1985 | European Pat. Off. . |
| 0 178 919 | 10/1985 | European Pat. Off. . |
| 0 180 994 | 11/1985 | European Pat. Off. . |
| 0 304 789 | 8/1988 | European Pat. Off. . |
| WO 92/08708 | 5/1992 | WIPO . |
| WO 93/23385 | 11/1993 | WIPO . |
| WO 93/24473 | 12/1993 | WIPO . |

OTHER PUBLICATIONS

"Synthesis and Evaluation of Non–Catechol D–1 and D–2 Dopamine Receptor Agonists: Benzimidazol–2–one, Benzoxazol–2–one, and the Hightly Potent Benzothiazol–2–one 7–Ethlamines" Joseph Weinstock et al., Journal Of Chemistry, vol. 30, pp. 1166–1176.

Primary Examiner—Michael G. Ambrose
Attorney, Agent, or Firm—Nixon & Vanderhye

[57] ABSTRACT

Compounds of formula I,

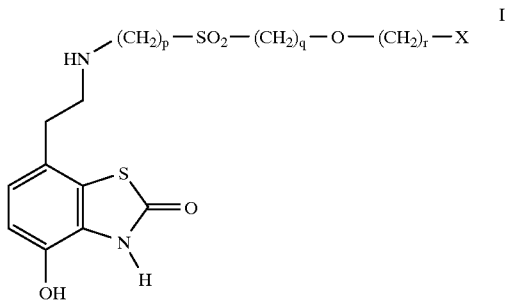

wherein
  X represents naphthyl optionally substituted by alkyl or halogen; and
  p, q and r independently represent 2 or 3,
  and pharmaceutically acceptable salts thereof;
processes for their preparation and methods for their use.

5 Claims, No Drawings

BIOLOGICALLY ACTIVE BENZOTHIAZOLONE ETHANAMINES

FIELD OF THE INVENTION

This invention relates to novel benzothiazolone ethanamines, processes for their preparation, pharmaceutical compositions containing them and methods of treatment involving their use. The novel compounds are indicated for use as dopamine $DA_2$-receptor agonists and $\beta_2$-adrenoreceptor agonists.

BACKGROUND

Benzothiazolone derivatives are known. For example, international patent applications, publication numbers WO92/08708 and WO93/23385 disclose biologically active amines, among them biologically active aminoethyl benzothiazolone derivatives which are $\beta_2$-adrenoreceptor agonists and dopamine $DA_2$-receptor agonists, and which are indicated in the treatment of reversible obstructive airways diseases.

WO 93/24473 discloses 7-(2-aminoethyl)-benzothiazolone compounds of formula

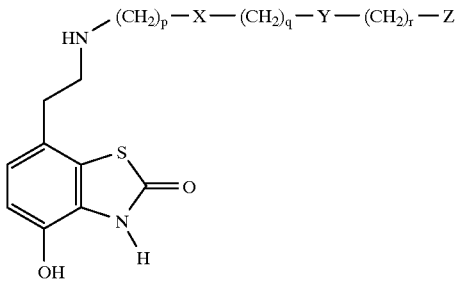

wherein X and Y are independently —S(O)$_n$— or —O—; n is 0,1 or 2; p, q and r are independently 2 or 3; Z is phenyl optionally substituted by halogen, OR$^1$, NO$_2$ or NR$^2$R$^3$; or Z is a 5 or 6 membered N, O or S containing heterocycle; and R$^1$, R$^2$ and R$^3$ are independently hydrogen or alkyl C$_{1-6}$. The compounds are $\beta_2$-adrenoreceptor agonists and dopamine $DA_2$-receptor agonists, and are indicated in the treatment of reversible obstructive airways diseases.

We have now found a group of novel benzothiazolone ethanamines which are indicated for use as dopamine $DA_2$-receptor agonists and $\beta$-adrenoreceptor agonists.

OUTLINE OF THE INVENTION

Accordingly, in one aspect of the present invention there are provided compounds of formula I,

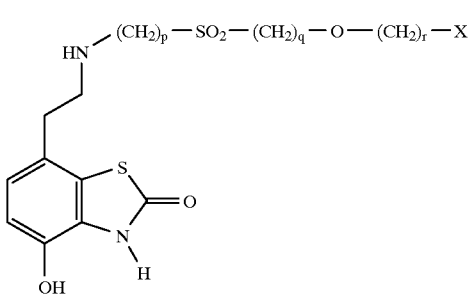

wherein

X represents naphthyl optionally substituted by alkyl or halogen; and p, q and r independently represent 2 or 3, and pharmaceutically acceptable salts thereof The compounds are pharmacologically active. They show both dopamine $DA_2$-receptor agonism and $\beta_2$-adrenoreceptor agonism. They exhibit little or no $\alpha_1$-adrenoreceptor agonism. The compounds have an advantageous duration of action and $DA_2/\beta_2$ ratio.

Preferably, p in formula I above is 3. q is preferably 2. r is preferably 2. X is preferably unsubstituted naphthyl.

Where X is alkyl-substituted naphthyl, the substituent may be selected from straight- or branched-chain C$_{1-6}$ alkyl, for example methyl, ethyl, n-propyl, i-propyl, n-butyl, i-butyl, straight- or branched-chain pentyl or straight or branched-chain hexyl. Preferred halogen substituents are F, Cl and Br. Where the alkyl substituent is chiral, optical isomers may be formed and are included in the scope of the present invention. Also included in the scope of the present invention are tautomers of the compounds of formula I.

Pharmaceutically acceptable salts of the compound of formula I include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, hydroxy-naphthalenecarboxylates, e.g. 1-hydroxy or 3-hydroxy-2-naphthalenecarboxylates, or oleates. The compounds may also form salts with suitable bases. The compound of formula I may be obtained in the form of a salt, conveniently a pharmaceutically acceptable salt. Where desired, such salts may be converted to the free bases using conventional methods. Pharmaceutically acceptable salts may be prepared by reacting the compound of formula I with an appropriate acid or base in the presence of a suitable solvent.

The present invention also provides a process for preparing compounds of formula I, comprising the selective reduction of a compound of formula II,

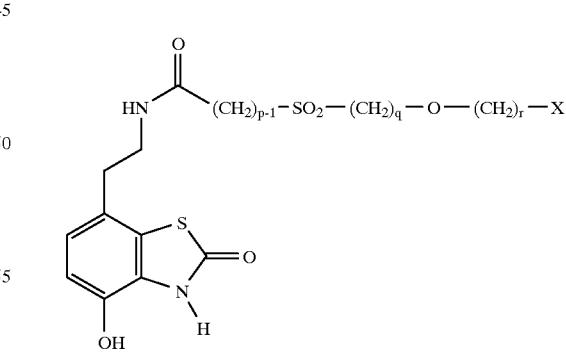

in which p, q, r, and X are as defined above.

Suitable reducing agents include electrophilic reducing agents, e.g., diborane and alane (aluminium hydride), or nucleophilic reducing agents, e.g., a complex metal hydride such as sodium bis(2-methoxyethoxy)aluminium hydride. The preferred reducing agent is diborane. The solvent should be inert to the reaction conditions. Aprotic solvents are preferred, e.g. tetrahydrofuran, diethyl ether, or 1,2- dimethoxyethane. The reaction may be carried out at a temperature of from about 0° C., to about 100° C., preferably at reflux temperature.

Compounds of formula II may be prepared by coupling an amine, of formula III:

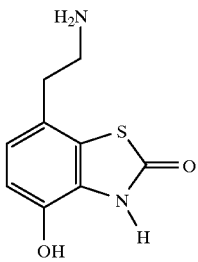

III and an appropriate acid, of formula IV $$HOOC—(CH_2)_{p-1}—SO_2—(CH_2)_q—O—(CH_2)_r—X \qquad IV$$

or corresponding acid chloride by conventional means. For example, the coupling may be performed in the presence of dicyclohexylcarbodiimide using the method of Sheehan and Hess, J. Am. Chem. Soc., 1955, 77, 1067; or 1,1'-carbonyldiimidazole as described by Staab, Angew. Chem. Int. Ed. Engl., 1962, 1, 351; or bromotripyrrolidinophosphonium hexafluorophosphate in a solvent such as DMF. The acids required for the process may be obtained from the corresponding esters, by hydrolysis with lithium hydroxide in aqueous methanol. The acid chlorides may be prepared from the acids for example by reaction with oxalyl chloride or thionyl chloride in toluene at a temperature from ambient to reflux. The compound of formula III may be prepared by known methods, for example by the method described in J. Med. Chem., 1987, 30, 1116.

Compounds of formula IV may be prepared as described in the Examples herein, which are easily adaptable by the person skilled in the art for the preparation of the range of compounds of formula IV.

In the above processes it may be necessary for any functional groups. e.g. hydroxy or amino groups, present in the starting materials to be protected. Suitable protecting groups and methods for their removal are, for example, those described in "Protective Groups in Organic Synthesis" by T. W. Greene and P. G. M. Wuts, John Wiley and Sons Inc., 1991.

Hydroxy groups may, for example, be protected by arylmethyl groups such as phenylmethyl, diphenylmethyl or triphenylmethyl, or as tetrahydropyranyl derivatives. Suitable amino protecting groups include arylmethyl groups such as benzyl, (R,S)-α-phenylethyl, diphenylmethyl or triphenylmethyl, and acyl groups such as acetyl, trichloroacetyl or trifluoroacetyl. Conventional methods of deprotection may be used. Arylmethyl groups may, for example, be removed by hydrogenolysis in the presence of a metal catalyst e.g. palladium on charcoal. Tetrahydropyranyl groups may be cleaved by hydrolysis under acidic conditions. Acyl groups may be removed by hydrolysis with a base such as sodium hydroxide or potassium carbonate, or a group such as trichloroacetyl may be removed by reduction with, for example, zinc and acetic acid.

The intermediates of formula II are novel, and are provided according to a further aspect of the present invention.

The compounds of formula I and salts thereof are dopamine $DA_2$-receptor agonists. The binding affinities of the test compounds for the $DA_2$ receptor binding sites in bovine pituitary membranes may be determined from the displacement of [$^3$H]-N-n-propylnorapomorphine and of [$^3$H]-spiperone in the absence or presence of nonhydrolysable GTP analogue respectively, D. R. Sibley, A. DeLean and I. Creese, Anterior Pituitary Dopamine Receptors, Demonstration of Interconvertible High and Low Affinity States of the D-2 Dopamine Receptor, J. Biol. Chem., 1982, 257(11), 6351–6361. The $DA_2$-receptor activity may also be demonstrated in a functional screen, the rabbit isolated ear artery, as described by Brown and O'Connor, Br. J. Pharmacol., 1981, 73, 189P. The compounds are also $\beta_2$-adrenoreceptor agonists. This activity may be demonstrated in the isolated trachea of the guinea pig, as described by I. G. Dougall, D. Harper, D. M. Jackson, and P. Leff, Br. J. Pharmacol., 1991, 104, 1057.

$\alpha_1$-Receptor activity may be analysed using the rabbit isolated ear artery screen described in the Examples.

The duration of action may be analysed following the method of Coleman et al., in "Novel and versatile superfusion system: its use in the evaluation of some spasmogenic and spasmolytic agents using guinea-pig isolated tracheal smooth muscle", Journal of Pharmacological Methods 21,71–86, (1989).

The compounds of formula I and salts thereof are indicated for use in the treatment of the range of airways diseases, including conditions such as asthma, including bronchial asthma, allergic asthma, intrinsic asthma (for example late asthma and airway hyper-responsiveness); and bronchitis and the like (see, for example, UK Patent No. 2022078 and Br. J. Pharmacol., 1987, 24, 4983).

The compounds of formula I and salts thereof are also indicated for use in the treatment of glaucoma and various other conditions, e.g. inflammatory and allergic skin disorders and cancer e.g. small cell lung cancer and congestive heart failure.

The term "treatment" as used herein includes prophylaxis as well as relief of the symptoms of disease.

Accordingly, in a further aspect of the present invention, there is provided the use of a compound of formula I, or a pharmaceutically acceptable salt thereof, in therapy.

Further, there is provided the use of a compound of formula I, or a pharmaceutically acceptable salt thereof, in the manufacture of a medicament for the treatment of airways disease, in particular for the treatment of asthma or chronic bronchitis.

Still further, the present invention provides a method of treatment of airways disease, which method comprises administering a therapeutically effective quantity of a compound of formula I, or a pharmaceutically acceptable salt thereof, to a patient suffering from or susceptible to such a condition.

According to a further aspect of the invention there is provided a method of treatment or prophylaxis of glaucoma, which method comprises administering a therapeutically effective quantity of the compound of formula I, or a pharmaceutically acceptable salt thereof, to a patient suffering from or susceptible to such a condition.

For the above mentioned uses the doses administered will, of course, vary with the mode of administration and the treatment desired. However, in general, satisfactory results are obtained when the compound of formula I is administered at a daily dosage of from about 1 µg to about 20 mg per kg of animal body weight, preferably given in divided doses 1 to 4 times a day or in sustained release form. For man the total daily dose is in the range of from 70 µg to 1,400 mg and unit dosage forms suitable for administration comprise from 20 µg to 1,400 mg of the compound admixed with a solid or liquid pharmaceutical diluent or carrier.

The compound of formula I may be used on its own or in the form of appropriate pharmaceutical compositions for topical, enteral or parenteral administration. For example metered dose inhaler devices may be used to administer the compound, dispersed in a suitable propellant and with or without additional excipients such as ethanol, surfactants, lubricants and stabilising agents.

Suitable propellants include hydrocarbon, chlorofluorocarbon and hydrofluoroalkane propellants, or mixtures of any such propellants. Especially preferred propellants are P134a and P227 each of which may be used alone or in combination with other propellants and/or surfactants and/or other excipients, for example in combination with each other.

Nebulised aqueous suspensions or, preferably, solutions may also be employed, with or without a suitable pH and/or tonicity adjustment, either as a unit-dose or multi-dose formulations.

Dry powder inhalers may be used to administer the compound, alone or in combination with a pharmaceutically acceptable carrier, in the latter case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

Tablets and gelatin capsules, which may be coated if desired, containing the active substance may, for example, also include one or more ingredient selected from diluents, carriers, binders, lubricants, stabilisers and other conventional ingredients.

Injectable solutions of the active ingredient may also contain, for example, one or more ingredient selected from preservatives, stabilisers, viscosity regulating agents, emulsifying agents, buffers and other conventional ingredients.

According to the invention there is also provided a pharmaceutical composition comprising, preferably less than 80% and more preferably less than 50% by weight of the compound of formula I, or a pharmaceutically acceptable salt thereof, in admixture with a pharmaceutically acceptable diluent or carrier.

The invention is illustrated, but in no way limited, by the following Examples, in which temperatures are in degrees Celsius.

EXAMPLE 1

4-Hydroxy-7-[2-[3-[2-[2-(1-naphthalenyl)ethoxy] ethylsulphonyl]propylamino]ethyl]-1,3-benzothiazol-2(3H)-one hydrochloride a) 1-[2-Ethenyloxy)ethyl]naphthalene A mixture of freshly distilled ethyl vinyl ether (60 ml), 2-(1-naphthalenyl)ethanol (8.61 g) and mercuric acetate (0.4 g) were heated at reflux for 20 hours. The volatile material was removed in vacuo (water pump) and the residue distilled by Kugelrohr to give the subtitled compound as an oil (8.15 g) which was contaminated with a small amount of 2-(1-naphthalenyl)ethanol.

bp 160–170° at 0.04 mm Hg;
Mass spectrum: gc/ms 198 (M), 155 (100).

b) Methyl 3-[2-[2-(1-naphthalenyl)ethoxy]ethylthio] propanoate

The product of step a) (8.15 g), methyl 3-mercaptopropanoate (4.86 g) and 2,2'-azobis(2-methylpropanonitrile) (0.2 g) were heated at 50° for 1 hour, after which time tlc indicated some starting material remained. A further quantity of 2,2'-azobis(2-methylpropanonitrile) (0.15 g) was added and the mixture heated at 60° for a further 1 hour. The crude reaction mixture was purified by flash chromatography (petrol:ether, 5:1 as eluant) to give the subtitled compound as a oil (11.07 g).

Mass spectrum: gc/ms 318 (M), 154 (100);
$^1$H nmr (360 mHz, CDCl$_3$) δ: 2.61 (2H, t), 2.72 (2H, t), 2.81 (2H, t), 3.38 (2H, t), 3.64 (2H, t), 3.70 (3H, s), 3.80 (2H, t), 7.40 (2H, m), 7.5 (2H m), 7.73 (1H, d), 7.85 (1H, d), 8.06 (1H, d).

c) Methyl 3-[2-[2-(1-naphthalenyl)ethoxy]ethylsulphonyl] propanoate

A solution of OXONE™ (18.4 g) in water (70 ml) was added dropwise at 10° to a solution of the product of step b) (3.18 g) in methanol (70 ml). The suspension was stirred at room temperature for 5 hours. The reaction mixture was diluted with water (200 ml) and extracted with dichloromethane (3×50 ml). The combined organic extracts were washed with water and sodium sulphite solution then dried and evaporated to give the subtitled compound (3.39 g) which was used in the next step without further purification.

Mass spectrum: gc/ms 350 (M), 154 (100);
$^1$H nmr (360 mHz, CDCl$_3$) δ: 2.70 (2H, t), 3.06 (2H, t), 3.17 (2H, t), 3.26 (2H, t), 3.71 (3H, s), 3.85 (4H, m), 7.40 (2H, m), 7.5 (2H), m), 7.73 (1H, d), 7.85 (1H, d), 8.06 (1H, d).

d) 3-[2-[2-(1-Naphthalenyl)ethoxy]ethylsulphonyl] propanoic acid

A solution of lithium hydroxide monohydrate (2.02 g) in water (30 ml) was added to a suspension of the product of step c) (3.35 g) in methanol (40 ml). The mixture was stirred at room temperature for 6 hours after which time tlc (ether) indicated that the ester had been consumed. The majority of the methanol was removed in vacuo and the residue diluted with water (100 ml). The basic solution was washed with ether. The aqueous layer was then acidified with hydrochloric acid and extracted with ether. The ether was washed with water, brine then dried (MgSO$_4$) and the solvent removed in vacuo to give the subtitled compound (3.08 g). This was further purified by flash chromatography (chloroform:acetic acid. 9:1 as eluant) to give the subtitled compound, after trituration with hexane, as a white solid (0.687 g).

mp 105–108°;
Mass spectrum: gc/ms 336 (M), 141 (100);
$^1$H nmr (360 mHz, CDCl$_3$) δ: 2.73 (2H, t), 3.15–3.22 (4H, m), 3.33–3.37 (2H, t), 3.79–3.86 (4H, m), 7.33–7.54 (4H, m), 7.72 (1H, d), 7.84 (1H, d), 8.00 (1H, d).

Analysis: Found C,60.90; H,6.34; S,9.48% Required C,60.70; H,5.99; S,9.53%.

e) N-[2-(4-Hydroxy-2-oxo-3H-1,3-benzothiazol-7-yl) ethyl]-3-[2-[2-(1-naphthalenyl)ethoxy]ethylsulphonyl] propanamide The product of step d) (0.625 g) was dissolved in dimethylformamide (10 ml) under nitrogen. To this stirred solution was added 1,1'-carbonyldiimidazole (0.301 g) and the mixture stirred for 2 hours at room temperature. 7-(2-Aminoethyl)-4-hydroxy-1,3-benzothiazol(3H)-2-one hydrobromide[1] (0.541 g) was added followed by triethylamine (0.259 ml). The mixture was stirred overnight then the volatiles were removed in vacuo. The residue was taken up into ethyl acetate and washed with dilute hydrochloric acid then brine. The organic layer was dried (MgSO$_4$) and the solvent removed in vacuo to give the subtitled compound (1.30 g) as an oil that was used without further purification.
[1]J. Med. Chem., 1987, 30, 1166.

Mass spectrum: FAB 529 (M+H).

f) 4-Hydroxy-7-[2-[3-[2-[2-(1-naphthalenyl)ethoxy] ethylsulphonyl]propylamino]ethyl]-1,3-benzothiazol-2 (3H)-one hydrochloride Borane-tetrahydrofuran solution (1.0 M in THF, 8.6 ml) was added dropwise to a stirred solution of the product of step e) (1.30 g) in dry tetrahydrofuran (100 ml). The reaction was then heated under reflux under an inert atmosphere for 1 hour. Reverse phase HPLC using acetonitrile and 0.1% trifluoroacetic acid as eluent showed a large amount of starting material remained so a further quantity of borane (8.6 ml) was added and the mixture heated under reflux for another 1 hour. The reaction was cooled and methanol (3.5 ml) was added cautiously. The solvents were removed in vacuo and the residue dissolved in methanol (100 ml) to which was added concentrated hydrochloric acid (sg. 1.18, 0.75 ml). This solution was heated at reflux for 20 min and then the solvent removed in vacuo. The residue was purified by preparative reverse phase HPLC using acetonitrile and 0.1% trifluoroacetic acid as eluent. Finally, preparation of the hydrochloride salt and recrystallisation from ethanol gave the title compound as a white powder (0.38 g).

mp 174–176°;

Mass spectrum: FAB 515 (M+H);

$^1$H nmr (360 mHz, $D_6$-DMSO) δ: 2.00–2.08 (2H, m), 2.86–2.91 (2H, m), 2.96 (2H, m), 3.06 (2H, m), 3.15 (2H, t), 3.33 (2H, t), 3.38–3.40 (2H, m), 3.76–3.82 (4H, m), 6.80 (1H, d), 6.89 (1H, d), 7.42–7.58 (4H, m), 7.80 (1H, d), 7.92 (1H, d), 8.09 (1H, d), 9.22 (2H, brs), 10.20 (1H, s), 11.82 (1H, s).

Analysis: Found C,56.16; H,5.98; N,5.40; S,11.77; Cl,6.00; $H_2O$,1.20% Required for 0.28 moles of water: C,56.16: H,5.89; N,5.04; S,11.52; Cl,6.39; $H_2O$,0.91%.

$DA_2$-receptor activity was demonstrated in a functional screen, the rabbit isolated ear artery, as described by Brown and O'Connor, Br. J. Pharmacol., 1981, 73, 189P.

$β_2$-adrenoreceptor activity was demonstrated in the isolated trachea of the guinea pig, as described by I. G. Dougall, D. Harper, D. M. Jackson, and P. Leff, Br. J. Pharmacol., 1991, 104, 1057.

$α_1$-Receptor activity was analysed using the rabbit isolated ear artery screen, as follows:

Rabbit Isolated Ear Artery

Male NZW rabbits (2.5–3.0 kg) were killed by intravenous injection of pentobarbitone sodium (60 mg/kg). The ears were removed and the proximal portion of the middle ear artery exposed and cannulated using a polypropylene cannula (0.75 mm external diameter). After removal, the artery was cleared of adherent connective tissue and 6 rings, 5 mm wide, were prepared preserving the plane of the circular smooth muscle. Tissues were mounted on fine tungsten wire hooks (0.25 mm diameter) in 20 ml organ baths containing Krebs solution of the following composition (mM): NaCl 117.56; $NaHCO_3$ 25.00; KCl 5.36; $NaH_2PO_4$ 0.89; $MgSO_4$ 1.18; glucose 11.10 and $CaCl_2$ 2.55. Cocaine (30 μM) and propanolol (1 μM) were included in the Krebs solution to block neuronal uptake and β-receptors respectively. Ascorbate (100 μM) was also added to prevent catecholamine oxidation. This solution was maintained at 37° C. and continuously gassed with 95% $O_2$: 5% $CO_2$. The upper wire hook was attached to an Ormed force displacement transducer, the lower hook being attached to a stationary support in the bath. Changes in isometric force were recorded on Advance Bryans AB500 flat-bed recorders.

Experimental

General

At the beginning of each experiment, a force of 1.0 g was applied to each tissue. This force was reinstated two or three times during a stabilisation period of approximately 60 min. until it remained constant. At the same time as the force was reinstated the baths were washed out. Agonist concentration-effect, E/[A], curves were constructed by cumulative additions of agonist at 0.5 $\log_{10}$ increments. Responses (contractions) were recorded as a percentage of the maximum response of the standard agonist.

Quantification of Agonism

Phenylephrine has been adopted as the standard agonist. An E/[A] curve to phenylephrine was constructed first. The phenylephrine was then washed out and an E/[A] curve to the test compound was constructed. Responses of compounds that produced agonism were expressed as a percentage of the maximum response to phenylephrine. The value of the asymptote of the test compound curve relative to phenylephrine indicated the intrinsic activity of the compounds. (Phenylephrine was assumed to have an intrinsic activity of 1).

The $p[A_{50}]$ value is a measure of agonist potency. It is the negative logarithm of the agonist concentration which produces a response that is half the maximum response. For compounds with intrinsic activities significantly less than 1, i.e. =<0.8, it is possible to calculate efficacy (τ) values and affinity ($pK_A$) values using the comparative method of analysis. This analysis assumes that phenylephrine is acting as a full agonist in this system and thus uses it to define the operational model parameters $E_m$ and n (ref Leff, et al., "Estimation of agonist affinity and efficacy by direct and operational model fitting.," J. Pharmacol. Methods., 1989, 23, 225–237). These parameters can then be utilised to perform a comparative analysis on the test compound to be made. Affinity is expressed as a $pK_A$ (the negative logarithm of the agonist concentration that occupies half of the receptors).

Quantification of Antagonism

Compounds that did not demonstrate agonism were investigated as antagonists by incubating tissues with as high a concentration of the compound as possible and subsequently constructing phenylephrine curves E/[A] curves. The degree of rightward shift of these phenylephrine curves compared to the control phenylephrine curve allowed an estimation of the affinity of a test compound to be made. Such affinity estimates are shown as $pA_2$ values (negative logarithm of the concentration of antagonist that produces a 2-fold rightward displacement of the control E/[A] curve).

Confirmation of $α_1$-mediated Agonism

Prazosin has been adopted as the standard $α_1$ antagonist. If a test compound showed agonism then, upon reaching the asymptote of the test compound E/[A] curve, prazosin (1 μM) was added to see if the response was reversed. If an $α_1$ antagonist reverses the response of the test compound this suggests that the agonism is $α_1$ mediated.

We claim:

1. A compound of formula I,

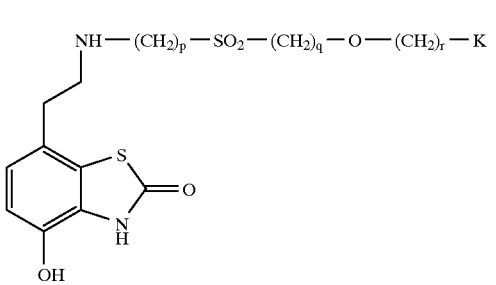

wherein

X represents naphthyl;

p is 3;

q is 2; and r is 2;

and pharmaceutically acceptable salts thereof.

2. A process for preparing a compound of formula I as defined in claim 1, comprising the selective reduction of a compound of formula II,

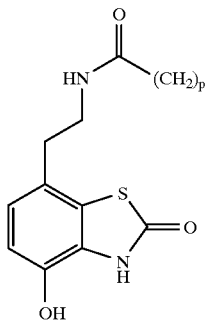

in which q, p, r and X are as defined in claim 1.

3. A compound of formula II,

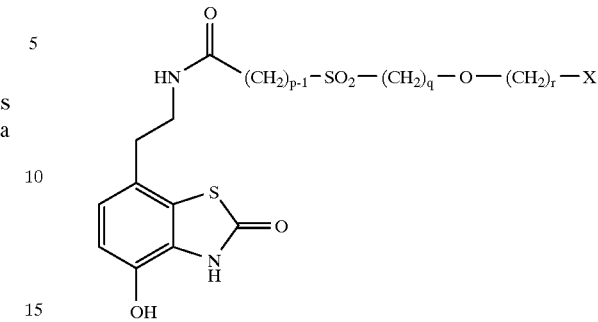

in which p, q, r and X are as defined in claim 1.

4. A method of treatment of airways disease, which method comprises administering a therapeutically effective quantity of a compound of formula I as defined in claim 1, or a pharmaceutically acceptable salt thereof, to a patient suffering from or susceptible to such a condition.

5. A method of treatment or prophylaxis of glaucoma, which method comprises administering a therapeutically effective quantity of a compound of formula I as defined in claim 1, or a pharmaceutically acceptable salt thereof, to a patient suffering from or susceptible to such a condition.

* * * * *